United States Patent [19]

Davis et al.

[11] Patent Number: 5,747,033
[45] Date of Patent: May 5, 1998

US005747033A

[54] METHOD OF ENHANCING THE BIOLOGICAL ACTIVITY OF EPH FAMILY LIGANDS

[75] Inventors: Samuel Davis, New York; Nicholas W. Gale, Dobbs Ferry; Thomas H. Aldrich, Ossining; Peter C. Maisonpierre, Croton, all of N.Y.; Mitchell Goldfarb, River Edge, N.J.; George D. Yancopoulos, Yorktown Heights, N.Y.

[73] Assignee: Regeneron Pharmaceuticals, Inc., Tarrytown, N.Y.

[21] Appl. No.: 299,567

[22] Filed: Sep. 1, 1994

Related U.S. Application Data

[63] Continuation-in-part of Ser. No. 229,402, Apr. 12, 1994, abandoned, which is a continuation-in-part of Ser. No. 222,075, Apr. 4, 1994, abandoned, which is a continuation-in-part of Ser. No. 144,992, Oct. 28, 1993, abandoned.

[51] Int. Cl.[6] .................. A61K 38/16; A61K 39/44; C07K 14/705; C07K 19/00
[52] U.S. Cl. .................. 424/134.1; 424/178.1; 424/143.1; 424/192.1; 424/156.1; 435/69.7; 435/172.1; 514/2; 530/350; 530/387.3; 530/839; 536/23.4

[58] Field of Search .................. 424/130.1, 139.1, 424/143.1; 435/7.1, 7.21, 244

[56] References Cited

U.S. PATENT DOCUMENTS 5,512,457  4/1996  Lyman et al. .................. 435/69.5

FOREIGN PATENT DOCUMENTS

| WO 92/07094 | 4/1992 | WIPO | C12Q 1/68 |
| WO 94/11020 | 5/1994 | WIPO | A61K 37/02 |
| WO 94/11384 | 5/1994 | WIPO | C07H 21/04 |

*Primary Examiner*—Lila Feisee
*Assistant Examiner*—John Lucas
*Attorney, Agent, or Firm*—Gail Kempler

[57] ABSTRACT

Novel ligands that bind Eph family receptors are identified, and methods for making the soluble ligands in biologically active form are described. cDNA clones encoding these novel proteins enable production of the recombinant proteins, which are useful to support neuronal and other receptor-bearing cell populations.

6 Claims, 9 Drawing Sheets

Fig.2.

```
B61                        meflwapl lglccslaaa DRHTVFWNSS NPKF-RNEDY    37
EHK1-L      maaapllllll llvpvpllpl laqgpggalg NRHAVYWNSS NDHL-RREGY    49
ELK-L       marpgqrwlg kwlvamvvwa lcrlatplaK NLEFVSWSSL NPKFLSGKGL     50
Consensus                                     V.WNSS NPKF.R.EGY       50

B61         TIHVQLNDYV DIICPHYEDH SV---ADAAM EDYLLYLVEH EEYQLCPQS      84
EHK1-L      TVQVNVNDYL DIMCPHYNSS GAGPGPGGGA EDYMLYMVSR NGYRTCNA-S     98
ELK-L       VIYPKIQDKL DIICPRAE-- -----AGRPY EMYKLYLVRP EQAAACSTVL     93
Consensus   TI.V...NDYL DIICPHYE.. .....AG... EDYL.LYLV.. E.Y..C...S    100

B61         KDQVRWQCNR PSAKHGPEKL SEKFQRFTPF TLGNEFKEGH YYYIDSK---    131
EHK1-L      QGFKRWECNR PHAPHSPIKF SEKFQRYSAF SLGYEFHAGH YYYISTT---   145
ELK-L       DPNVLVTCNR PEQE---IRF TIKFQEFSPN YMGLEFKKHH DYYITSTSNG    140
Consensus   ...VRW.CNR P.A.H.PIKF SEKFQRFSPF .LG.EFK.GH .YYYIST...    150

B61         PIHQHEDR-- --C-LR-LKV TV-SGKITHS PQAHVNPQEK RLAADDPEVR    174
EHK1-L      PTHNLHWK-- --C-LR-MKV FVCCASTSHS GEKPVPTLPQ FTMGPNVKIN    189
ELK-L       SLEGLENREG GVCRTRTMKI IMKVGQDPNA VTPEQLTTSR PSKEADNTVK    190
Consensus   P.H.LE.R.. ..C.LR.MK                                       200

B61         VLHSIGHSAA PRlfplawtv lllplllqtp                            206
EHK1-L      VLEDFEGENP QVPKLEKSIS GTSPKREHlp lavgiafflm tflas            234
ELK-L       MATQAPGSRG SLGDSDGKHE TVNQEEKSGP GASGGSSGDP DGFFNSKval     237

ELK-L       faavgagcvi flliiifltv lllKLRKRHR KHTQQRAAAL SLSTLASPKG     297

ELK-L       GSGTAGTEPS DIIIPLRTTE NNYCPHYEKV SGDYGHPVYI VQEMPPQSPA     347

ELK-L       NIYYKV                                                      353
```

Fig.3.

NUCLEOTIDE SEQUENCE OF CODING REGION OF EHK-1L

GAC CTC GAG ATC CAT TGT GCT GGA AAG GCG GCG GCG GCT CCG GGG ATG GCG
GCG GCT CCG CTG CTG CTG CTG CTG CTG CTC GTG CCC GTG CCG CTG CTG CCG CTG CTG
GCC CAA GGG CCC GGA GGG GCG CTG GGA AAC CGG CAT GCG GTG TAC TGG AAC
AGC TCC AAC CAG CAC CTG CGG CGA GAG GGC TAC ACC GTG CAG GTG AAC GTG AAC
GAC TAT CTG GAT ATT TAC TGC CCG CAC TAC AAC AGC TCG GGG GCG GGA CCG GGG
CCC GGA GGC GGG GCA GAG CAG TAC GTG CTG TAC ATG GTG AGC CGC AAC GGC
TAC CGC ACC TGC AAC GCC AGC CAG GGC TTC AAG CGC TGG GAG TGC AAC CGG
CCG CAC GCC CCG CAC AGC CCC ATC AAG TTC TCG GAG AAG TTC CAG CGC TAC AGC GCC
TTC TCT CTG GGC TAC GAG TTC CAC GCC GGC CAC GAG TAC TAC TAC ATC TCC ACG
CCC ACT CAC AAC CTG CAC TGG AAG TGT CTG AGG ATG AAG GTG TTC GTC TGC
TGC GCC TCC ACA TCG CAC TCC GGG GAG AAG CCG GTC CCC ACT CTC CCC CAG TTC
ACC ATG GGC CCC AAT GTG AAG ATC AAC GTG CTG GAA GAC TTT GAG GGA GAG AAC
CCT CAG GTG CCC AAG CTT GAG AAG AGC ATC AGC GGG ACC AGC CCC AAA CGG
GAA CAC CTG CCC CTG GCC GTG GGC ATC GCC TTC TTC CTC ATG ACG TTC TTG GCC
TCC TAG CTC TGC CCC CTC CCC TGG GGG GGG AGA GAT GGG GCG GGG NTT GGA AGG
AGN AGG GAG CCT TTG GCC TCT CCA AGG GAA GCC TAG TGG GCC TAG ACC CCT CCT
CCC ATG GTT AGA AGT GGG GCC TGN ACC ATA CAT CTG TGT CCG CCC CCT CTA CCC
CTT CCC CCC ANG TAG GGN ACT GTA GTG GAC CAA GCA CGG NGA CAG ACA TGG
NTC CCG GGN GGG CTT GTG GCT CTG GTA ATG TNT GGC ACC AAA CTT GGG GGG CAA
AAA GGG GAG TGC TCA GGA CTC CCT GGN CCC TGG TAC TTT CCC TGA ATC TGG TGC
CTC TC

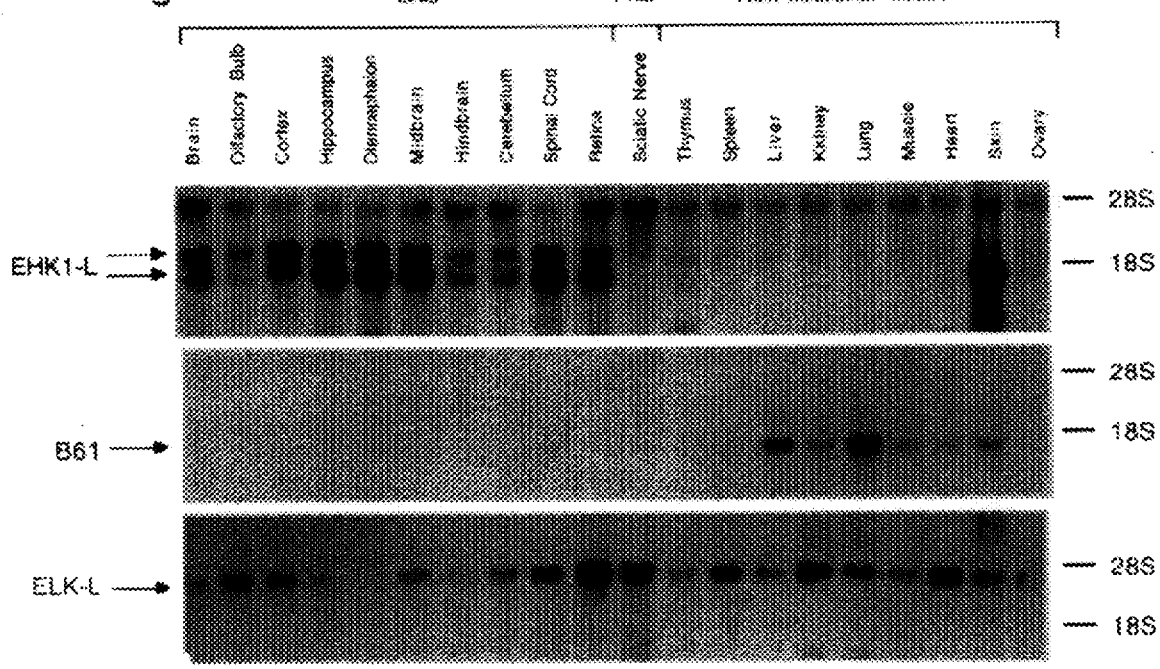

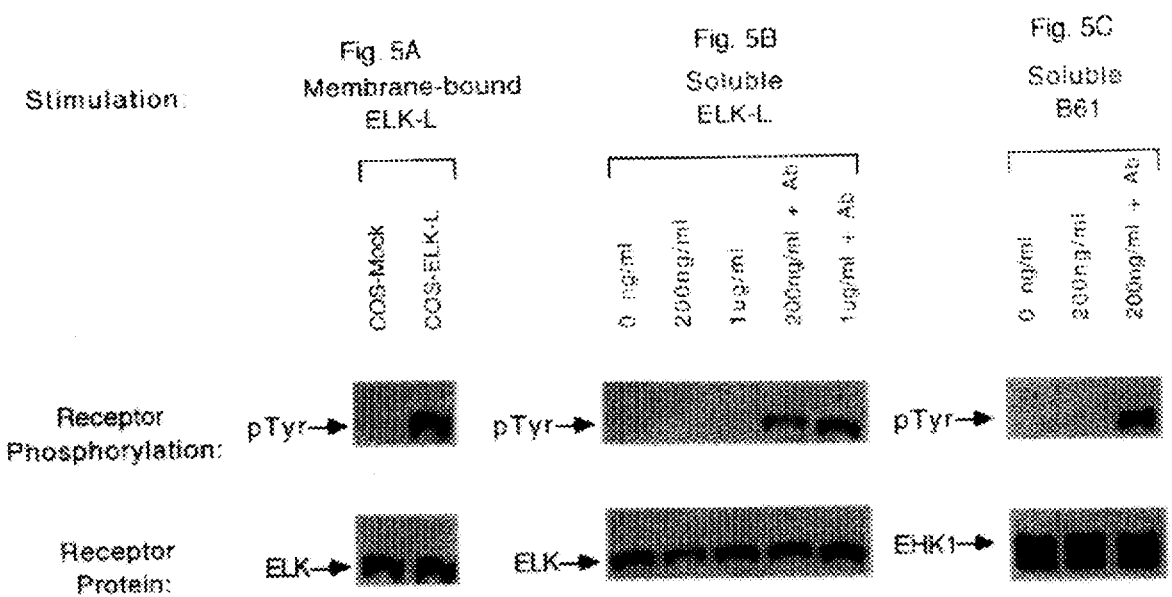

METHOD OF ENHANCING THE BIOLOGICAL ACTIVITY OF EPH FAMILY LIGANDS

This application is a continuation-in-part of U.S. patent application Ser. No. 08/229,402 filed on Apr. 12, 1994 entitled "Eph Family Ligands" now abandoned which is a continuation-in-part of U.S. patent application Ser. No. 08/222,075 filed on Apr. 4, 1994 entitled "Ehk-1 Binding Ligands" now abandoned which is a continuation-in-part of U.S. patent application Ser. No. 08/144,992 filed on Oct. 28, 1993 entitled "Assay Systems for Neurotrophin Activity" now abandoned.

INTRODUCTION

The present invention provides for novel ligands that bind proteins belonging to the Eph subfamily of receptorlike protein tyrosine kinases, such as the Ehks (including Ehk-1, Ehk-2 and Ehk-3), Eck, and Elk and methods for making soluble forms of these ligands that are biologically active.

BACKGROUND OF THE INVENTION

The ability of polypeptide ligands to bind cells and thereby elicit a phenotypic response such as cell growth, survival or differentiation is often mediated through transmembrane tyrosine kinases. The extracellular portion of each receptor tyrosine kinase (RTK) is generally the most distinctive portion of the molecule, as it provides the protein with its ligand-recognizing characteristic. Binding of a ligand to the extracellular domain results in signal transduction via an intracellular tyrosine kinase catalytic domain which transmits a biological signal to intracellular target proteins. The particular array of sequence motifs of this cytoplasmic, catalytic domain determines its access to potential kinase substrates (Mohammadi, et al.,1990, Mol. Cell. Biol., 11:5068–5078; Fantl, et al., 1992, Cell, 69:413—413).

RTKs appear to undergo dimerization or some related conformational change following ligand binding (Schlessinger, J., 1988, Trend Biochem. Sci. 13:443–447; Ullrich and Schlessinger, 1990, Cell, 61:203–212; Schlessinger and Ullrich, 1992, Neuron 9:383–391); molecular interactions between dimerizing cytoplasmic domains lead to activation of kinase function. In some instances, such as the growth factor platelet derived growth factor (PDGF), the ligand is a dimer that binds two receptor molecules (Hart, et al. , 1988, Science, 240:1529–1531; Heldin, 1989, J. Biol. Chem. 264:8905–8912) while, for example, in the case of EGF, the ligand is a monomer (Weber, et al., 1984, J. Biol. Chem., 259:14631–14636).

The tissue distribution of a particular tyrosine kinase receptor within higher organisms provides relevant data as to the biological function of the receptor. The tyrosine kinase receptors for some growth and differentiation factors, such as fibroblast growth factor (FGF) are widely expressed and therefore appear to play some general role in tissue growth and maintenance. Members of the Trk RTK family (Glass & Yancopoulos, 1993, Trends in Cell Biol, 3:262–268) of receptors are more generally limited to cells of the nervous system, and the Nerve Growth Factor family consisting of NGF, BDNF, NT-3 and NT-4/5 (known as the neurotrophins) which bind these receptors promote the differentiation of diverse groups of neurons in the brain and periphery (Lindsay, R. M, 1993, in Neurotrophic Factors, S. E. Loughlin & J. H. Fallon, eds., pp. 257–284 (San Diego, Calif.: Academic Press). The localization of one such Trk family receptor, trkB, in tissue provided some insight into the potential biological role of this receptor, as well as the ligands that bind this receptor (referred to herein as cognates). Thus, for example, in adult mice, trkB was found to be preferentially expressed in brain tissue, although significant levels of trkB mRNAs were also observed in lung, muscle, and ovaries. Further, trkB transcripts were detected in mid and late gestation embryos. In situ hybridization analysis of 14 and 18 day old mouse embryos indicated that trkB transcripts were localized in the central and peripheral nervous systems, including brain, spinal cord, spinal and cranial ganglia, paravertebral trunk of the sympathetic nervous system and various innervation pathways, suggesting that the trkB gene product may be a receptor involved in neurogenesis and early neural development as well as play a role in the adult nervous system.

The cellular environment in which an RTK is expressed may influence the biological response exhibited upon binding of a ligand to the receptor. Thus, for example, when a neuronal cell expressing a Trk receptor is exposed to a neurotrophin which binds that receptor, neuronal survival and differentiation results. When the same receptor is expressed by a fibroblast, exposure to the neurotrophin results in proliferation of the fibroblast (Glass, et al., 1991, Cell 66:405–413). Thus, it appears that the extracellular domain provides the determining factor as to the ligand specificity, and once signal transduction is initiated the cellular environment will determine the phenotypic outcome of that signal transduction.

A number of RTK families have been identified based on sequence homologies in their intracellular domain. The receptor and signal transduction pathways utilized by NGF involves the product of the trk proto-oncogene (Kaplan et al., 1991, Nature 350:156–160; Klein et al., 1991, Cell 65:189–197). Klein et al. (1989, EMBO J. 8:3701–3709) reported the isolation of trkB, which encodes a second member of the tyrosine protein kinase family of receptors found to be highly related to the human trk protooncogene. TrkB binds and mediates the functional responses to BDNF, NT-4, and, to a lesser extent, NT-3 (Squinto, et al., 1991, Cell 65:885–903; lp, et al., 1992, Proc. Natl. Acad. Sci. U.S.A. 89:3060–3064; Klein, et al., 1992, Neuron, 8:947–956). At the amino acid level, the products of trk and trkB were found to share 57 percent homology in their extracellular regions, including 9 of the 11 cysteines present in trk. This homology was found to increase to 88 percent within their respective tyrosine kinase catalytic domains. The Trk gene family has now been expanded to include the trkC locus, with NT-3 having been identified as the preferred ligand for trkC (Lamballe, et al., 1991, Cell 66:967–979; Valenzuela, et al. 1993, Neuron 10:963–974).

The Eph-related transmembrane tyrosine kinases comprise the largest known family of receptor-like tyrosine kinases, with many members displaying specific expression in the developing and adult nervous system. Two novel members of the Eph RTK family, termed Ehk (eph homology kinase) -1 and -2 were identified using a polymerase chain reaction (PCR)-based screen of genes expressed in brain (Maisonpierre, et al. 1993, Oncogene 8:3277–388). These genes appear to be expressed exclusively in the nervous system, with Ehk-1 expression beginning early in neural development. Recently, a new member of this group of related receptors, Ehk-3 has been cloned (Valenzuela, et al. in press).

The elk gene encodes a receptorlike protein-tyrosine kinase that also belongs to the eph subfamily, and which is expressed almost exclusively in the brain (and at lower levels in the testes) (Letwin, et al. 1988; Oncogene 3:621–678; Lhotak, et al., 1991 Mol. Cell. Biol. 11:2496–2502. Based on its expression profile cognate ligand are expected to play a role in cell to cell interactions in the nervous system.

Unlike the Ehks and Elk receptors, the closely related Eck receptor appears to function in a more pleiotrophic manner; it has been identified in neural, epithelial and skeletal tissues and it appears to be involved in the gastrulation, craniofacial, and limb bud sites of pattern formation in the mouse embryo (Ganju, et al. 1994, Oncogene 9:1613–1624).

The identification of a large number of receptor tyrosine kinases has far exceeded the identification of their cognate ligands. At best, determination of the tissues in which such receptors are expressed provides insight into the regulation of the growth, proliferation and regeneration of cells in target tissues. Because RTKs appear to mediate a number of important functions during development, their cognate ligands will inevitably play a crucial role in development.

In copending U.S. patent application Ser. No. 08/144,992 filed on Oct. 28, 1993, which is incorporated in its entirely herein, a number of orphan tyrosine kinase receptor-like molecules, including five such molecules that are homologous to trk receptor and the insulin receptor family, and another four molecules that are homologous to, respectively, CSF1R/PDGFR/kit; ret; eck-alpha (now known as Ehk-2); and eck beta (Ehk-1) are described. In that application, methods were described wherein cell lines expressing Ehk-1 and Ehk-2 were used to assay for identifying their cognate ligands. Because the ehks appear to be expressed in distinctive neuronal populations, including some of the principal ascending central cholinergic nuclei, ligands which bind these receptors were expected to play a role in promoting the growth or survival of these neuronal cells. Because the expression of Ehk-1 begins early in development, its cognate ligands may play a role in embryogenesis.

Although a number of schemes have been devised for the identification of cognate ligands for the many orphan receptors that have been identified, very few such ligands have been identified, and the ligands that have been identified to date appear to have no activity other than the ability to bind their cognate receptor. For example, International Publication Number WO/94/11020 published on May 26, 1994 describes ligands that bind to the Eck receptor. In particular the ligand EBP (also known as B61) is described. However, although binding of B61 to the Eck receptor is disclosed, no biological activity is described. Similarly, despite the description in PCT Publication Number WO94/11384 (published May 26, 1994) of a ligand that binds the Elk receptor, no biological activity was observed, regardless of whether the ligand was presented as membrane bound or in the form of an Fc dimer of the soluble ligand. With respect to the Elk receptor, however, chimeric EGFR-Elk receptors (having the extracellular domain of the EGFR fused to the Elk cytoplasmic domain) have been used to demonstrate the functional integrity (as measured by EGF-stimulated autophosphorylation) of the enzymatic domain of this receptor. (Lhotak and Pawson 1993, Mol. Cell. Biol. 13:7071–7079).

SUMMARY OF THE INVENTION

The present invention provides for novel polypeptide ligands that bind to the Ehk-1, Ehk-2 and Ehk-3, Eck and Elk receptors on cells. More importantly, the invention provides a means of making biologically active, soluble forms of these ligands, which are useful in promoting a differential function and/or influencing the phenotype, such as growth and/or proliferation, of receptor bearing cells. The invention also provides for nucleic acids encoding such polypeptide ligands, and both prokaryotic and eukaryotic expression systems for producing such proteins. The invention also provides for antibodies to these ligands.

According to the invention, soluble forms of the ligands described herein may be used to promote biological responses in Ehk-1, Ehk-2, Ehk-3, Eck and Elk receptor-expressing cells. In particular, a general method is described herein which produces "clustering" of ligands for eph-related receptors, which functions to make otherwise inactive soluble ligands biologically active, or which enhances the biological activity of ligands that, absent such clustering, would have only low levels of biological activity.

The ligands described herein also have diagnostic utilities. In particular embodiments of the invention, methods of detecting aberrancies in their function or expression may be used in the diagnosis of neurological or other disorders. In other embodiments, manipulation of the interaction between the ligands and their cognate receptor may be used in the treatment of neurological or other disorders.

DESCRIPTION OF THE FIGURES

FIG. 2. Sequence comparison of ligands for Ehk-1 and Elk receptors. Aligned sequences of B61 (SEQ ID NO:4), Ehk-1 ligand (EHK-1L) (SEQ ID NO:5) and Elk ligand (ELK-L) (SEQ ID NO:6) are displayed. Residues shared by all three sequences are boxed, and residues shared by at least two are shown in the Consensus lane (SEQ ID NO:7); bold dots indicate conserved cysteines, and asterisks demarcate residues bordering main conserved regions. Lower case letters show the presumed amino-terminal signal sequences as well as the transmembrane domain of ELK-L and carboxy-terminal hydrophobic GPI-recognition tails of B61 and EHK1-L.

FIG. 3. Nucleotide sequence of EHK-1L coding region (SEQ ID NO:8).

FIG. 5. Activation of Eph family receptors by membrane-bound or clustered ligands as measured by Elk receptor tyrosine phosphorylation. FIG. 5A: Stimulation using control COS cells transfected with vector alone (COS-Mock) or COS cells transfected with an expression construct encoding Efl-3 (ELK-L); FIG. 5B: Stimulation with soluble myc-tagged Efl-3 (ELK-L), used as an unclustered ligand (second and third wells) or ligand clustered by antibodies (forth and fifth wells). ("+Ab" denotes soluble ligands clustered with antibody). Control (0 ng/ml) is shown in first well. FIG. 5C: Stimulation with soluble myc-tagged Efl-1 (B61), used as an unclustered ligand (second well) or ligand clustered by antibodies (third well). Control (0 ng/ml) is shown in first well. Upper panels in FIGS. A, B and C show immunoprecipitates immunoblotted with antibodies to phosphotyrosine. Lower panels in FIGS. A, B and C show immunoprecipitates that were subsequently stripped and reprobed with antibodies recognizing the receptors to visualize total receptor protein.

DETAILED DESCRIPTION OF THE INVENTION

Figure 1:
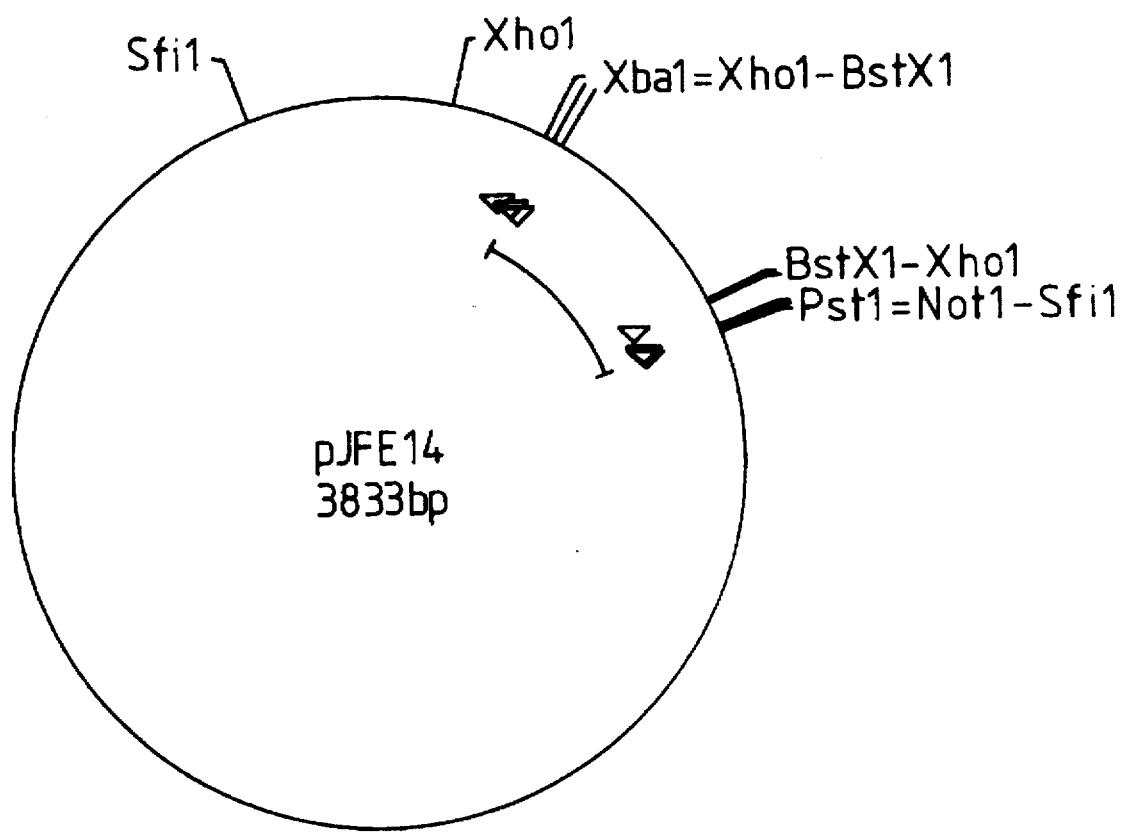
FIG. 1. Vector pJFE14.

The utilization of assay systems utilizing the Ehk-1, Ehk-2, Ehk-3, Eck and Elk receptors has led to the discovery, as described herein, of cognate ligands to these receptors. Such ligands are useful for promoting the growth and survival of neuronal, epithelial, or other receptor-bearing cell populations in vitro.

As described in greater detail below, applicants have discovered, by expression cloning, one or more novel ligands that bind the Ehk-1 and Elk receptors. In addition, applicants have discovered that the previously identified ligand B61 (Holzman, et al., 1990, Mol. Cell. Biol. 10:5830–5838) also binds to Ehk-1 and that both B61 and the Ehk-1 ligand also bind the Ehk-2 and newly discovered Ehk-3 receptor, and well as the Eck receptor.

The novel ligands described herein are designated as Efl's (Eph transmembrane tyrosine kinase family ligands). The novel Ehk-1 binding ligands Efl-1 and Efl-2, which were originally described in copending U.S. patent application Ser. Nos. 08/229,402 filed on Apr. 12, 1994 and 08/225,075 filed on Apr. 4, 1994 are identical and are redesignated herein as Efl-2. B61 has now been designated as Efl-1. The amino acid sequences of B61 (Efl-1) and EHK-1L (Efl-2), as well as the sequence of the Elk binding ligand Efl-3, which was described in copending application 08/229,402 and published in PCT/US93/10879; published as WO 94/11020 on May 26, 1994, are set forth in FIG. 2.

When used herein, Efl-1, Efl-2 and Efl-3 include functionally equivalent molecules in which amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the invention are proteins or fragments or derivatives thereof which exhibit the same or similar biological activity and derivatives which are differentially modified during or after translation, e.g., by glycosylation, proteolytic cleavage, linkage to an antibody molecule or other cellular ligand, etc.

Cells that express Efl's may do so naturally or may be genetically engineered to produce these ligands, as described supra, by transfection, transduction, electroporation, microinjection, via a transgenic animal, etc. of nucleic acid encoding the Efls described herein in a suitable expression vector. Vectors containing the cDNA encoding for EFl-2 (EHK-1L) were deposited with the American Type Culture Collection under the terms of the Budapest Treaty on Apr. 4, 1994 as pJFE14 containing Ehk-1L2B4 and Ehk-1L3B1 and have been given the ATCC designations 75728 and 75729 respectively. (The ligands encoded by these vectors are identical). The pJFE14 vector containing the cDNA encoding for Efl-3 (ELK-L) was deposited with the American Type Culture Collection under the terms of the Budapest Treaty on Apr. 12, 1994 as pJFE14 containing efl-3 and has been given the ATCC designation 75734.

The present invention encompasses the DNA sequence contained in the above deposited plasmids, as well as DNA and RNA sequences that hybridize to the Efl sequences contained therein, under conditions of moderate stringency, as defined in, for example, Sambrook, et al. Molecular Cloning: A Laboratory Manual, 2 ed. Vol. 1, pp. 101–104, Cold Spring Harbor Laboratory Press (1989). Thus, nucleic acids contemplated by the invention include the sequences as contained in the deposits, sequences of nucleic acids that hybridize to such sequences and which bind the Ehk-1, Ehk-2, Ehk-3, Eck or Elk receptor, and nucleic acid sequences which are degenerate of the above sequences as a result of the genetic code, but which encode ligand(s) that binds the Ehk-1, Ehk-2, Ehk-3, Eck or Elk receptor.

In addition, the present invention contemplates use of the ligands described herein in soluble forms, truncated forms, and tagged forms.

Any of the methods known to one skilled in the art for the insertion of DNA fragments into a vector may be used to construct expression vectors encoding Efl's using appropriate transcriptional/translational control signals and the protein coding sequences. These methods may include in vitro recombinant DNA and synthetic techniques and in vivo recombinations (genetic recombination). Expression of nucleic acid sequence encoding the Efl's or peptide fragments thereof may be regulated by a second nucleic acid sequence so that the protein or peptide is expressed in a host transformed with the recombinant DNA molecule. For example, expression of the Efl's described herein may be controlled by any promoter/enhancer element known in the art. Promoters which may be used to control expression of the ligands include, but are not limited to the long terminal repeat as described in Squinto et al., (1991, Cell 65:1–20); the SV40 early promoter region (Bernoist and Chambon, 1981, Nature 290:304–310), the CMV promoter, the M-MuLV 5' terminal repeat the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:144–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25), see also "Useful proteins from recombinant bacteria" in Scientific American, 1980, 242:74–94; promoter elements from yeast or other fungi such as the Gal 4 promoter, the ADH (alcohol dehydrogenase) promoter, PGK (phosphoglycerol kinase) promoter, alkaline phophatase promoter, and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538;

Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58); alpha 1-antitrypsin gene control region which is active in the liver (Kelsey et al, 1987, Genes and Devel. 1:161–171), beta-globin gene control region which is active in myeloid cells (Mogram et al., 1985, Nature 315:338–340; Kollias et al., 1986, Cell 46:89–94); myelin basic protein gene control region which is active in oligodendrocyte cells in the brain (Readhead et al., 1987, Cell 48:703–712); myosin light chain-2 gene control region which is active in skeletal muscle (Shani, 1985, Nature 314:283–286), and gonadotropic releasing hormone gene control region which is active in the hypothalamus (Mason et al., 1986, Science 234:1372–1378).

Thus, according to the invention, expression vectors capable of being replicated in a bacterial or eukaryotic host comprising Efl-encoding nucleic acid as described herein, are used to transfect the host and thereby direct expression of such nucleic acid to produce the Efl proteins, which may then be recovered in biologically active form. As used herein, a biologically active form includes a form capable of binding to the relevant receptor, such as Ehk-1 or Elk, and causing a differentiated function and/or influencing the phenotype of the cell expressing the receptor. Such biologically active forms would, for example, induce phosphorylation of the tyrosine kinase domain of the Ehk-1 or Elk receptor, or stimulation of synthesis of cellular DNA.

Expression vectors containing the gene inserts can be identified by three general approaches: (a) DNA—DNA hybridization, (b) presence or absence of "marker" gene functions, and (c) expression of inserted sequences. In the first approach, the presence of a foreign gene inserted in an expression vector can be detected by DNA—DNA hybridization using probes comprising sequences that are homologous to an inserted efl gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if the efl gene is inserted within the marker gene sequence of the vector, recombinants containing the insert can be identified by the absence of the marker gene function. In the third approach, recombinant expression vectors can be identified by assaying the foreign gene product expressed by the recombinant. Such assays can be based, for example, on the physical or functional properties of the efl gene product, for example, by binding of the ligand to the Ehk-1 or Elk receptor or portion thereof which may be tagged with, for example, a detectable antibody or portion thereof or binding to antibodies produced against the Efl protein or a portion thereof.

The Efl-2 (EHK-1L) ligand appears to have some homology with the previously identified ligand B61 (referred to herein as Efl-1). [Holzman, et al., 1990, Mol. Cell. Biol. 10:5830–5838). Like B61, Efl-2 ends in a C-terminal hydrophobic sequence that appears to encode a recognition sequence allowing it to be GPI-linked and thus lacking in an intracellular domain. In fact, pretreatment of Efl-2 expressing cells with phospholipase C appears to reduce Ehk-1 receptorbody binding, thus confirming that these proteins are PI-linked. Efl-3 is not cleaved from the cell surface using phospholipase C and it appears to comprise a conventional transmembrane protein with a cytoplasmic domain.

The ligands described herein may be produced as membrane bound forms in animal cell expression systems or may be expressed in soluble form. Soluble forms of the ligands may be expressed using methods known to those in the art. A commonly used strategy involves use of oligonucleotide primers, one of which spans the N-terminus of the protein, the other of which spans the region just upstream to a hydrophobic segment of the protein, which represents either the GPI-linkage recognition domain or a transmembrane domain of the protein. The oligonucleotide spanning the C-terminus region is modified so as to contain a stop codon prior to the hydrophobic domain. The two oligonucleotides are used to amplify a modified version of the gene encoding a protein that is secreted instead of membrane bound. Alternatively, a convenient restriction site in the vector can be used to insert an altered sequence that removes the GPI-linkage recognition domain or transmembrane domain, thus resulting in a vector capable of expressing a secreted form of the protein. The soluble protein so produced would include the region of the protein from the N-terminus to the region preceding the hydrophobic GPI recognition domain or transmembrane domain.

Applicants have discovered that although the soluble ligands produced according to the invention bind to the receptors in the eph subfamily, such soluble ligands often have little or no biological activity. Such soluble ligands are activated, according to the present invention, by ligand "clustering". "Clustering" as used herein refers to any method known to one skilled in the art for creating multimers of the soluble portions of ligands described herein.

In one embodiment, a "clustered" efl is a dimer, made for example, according to the present invention utilizing the Fc domain of IgG (Aruffo et al., 1991, Cell 67:35–44), which results in the expression of the soluble ligand as a disulfide-linked homodimer. In another embodiment, secreted forms of the ligands are constructed with epitope tags at their C-termini; anti-tag antibodies are then used to aggregate the ligands.

In addition, the invention contemplates other "engineered" ligand molecules that exist as or form multimers. For example, dimers of the extracellular domains may be engineered using leucine zippers. The leucine zipper domains of the human transcription factors c-jun and c-fos have been shown to form stable heterodimers [Busch and Sassone-Corsi, Trends Genetics 6:36–40 (1990); Gentz et al., Science 243:1695–1699 (1989)] with a 1:1 stoichiometry. Although jun—jun homodimers have also been shown to form, they are about 1000-fold less stable than jun-fos heterodimers. Fos—fos homodimers have not been detected. The leucine zipper domain of either c-jun or c-fos are fused in frame at the C-terminus of the soluble or extracellular domains of the above mentioned ligands by genetically engineering chimeric genes. The fusions may be direct or they may employ a flexible linker domain, such as the hinge region of human IgG, or polypeptide linkers consisting of small amino acids such as glycine, serine, threonine or alanine, at various lengths and combinations. Additionally, the chimeric proteins may be tagged by His—His—His—His—His—His (His6) (SEQ ID NO:1), to allow rapid purification by metal-chelate chromatography, and/or by epitopes to which antibodies are available, to allow for detection on western blots, immunoprecipitation, or activity depletion/blocking in bioassays.

Alternatively, multimers may be made by genetically engineering and expressing molecules that consist of the soluble or extracellular portion of the ligand followed by the Fc-domain of hIgG, followed by either the c-jun or the c-fos leucine zippers described above [Kostelny et al., J. Immunol. 148:1547–1553 (1992)]. Since these leucine zippers form predominately heterodimers, they may be used to drive formation of the heterodimers where desired. As for the chimeric proteins described using leucine zippers, these may also be tagged with metal chelates or an epitope. This tagged domain can be used for rapid purification by metal-chelate chromatography, and/or by antibodies, to allow for detection on western blots, immunoprecipitation, or activity depletion/ blocking in bioassays.

In another embodiment of the invention, multimeric soluble ligands are prepared by expression as chimeric molecules utilizing flexible linker loops. A DNA construct encoding the chimeric protein is designed such that it expresses two or more soluble or extracellular domains fused together in tandem ("head to head") by a flexible loop. This loop may be entirely artificial (e.g. polyglycine repeats interrupted by serine or threonine at a certain interval) or "borrowed" from naturally occurring proteins (e.g. the hinge region of hIgG). Molecules may be engineered in which the length and composition of the loop is varied, to allow for selection of molecules with desired characteristics. Although not wishing to be bound by theory, applicants believe that membrane attachment of the ligands facilitates ligand clustering, which in turn promotes receptor multimerization and activation. Thus, according to the invention, biological activity of the soluble ligand is achieved by mimicking, in solution, membrane associated ligand clustering. Thus, a biologically active, clustered soluble eph family ligand comprises (soluble Efl)$_n$, wherein the soluble efl is the extracellular domain of a ligand that binds an eph family receptor and n is 2 or greater. As described herein, Efl-1, Efl-2 and Efl-3 are all made biologically active according to the process of the invention.

Figure 6A:
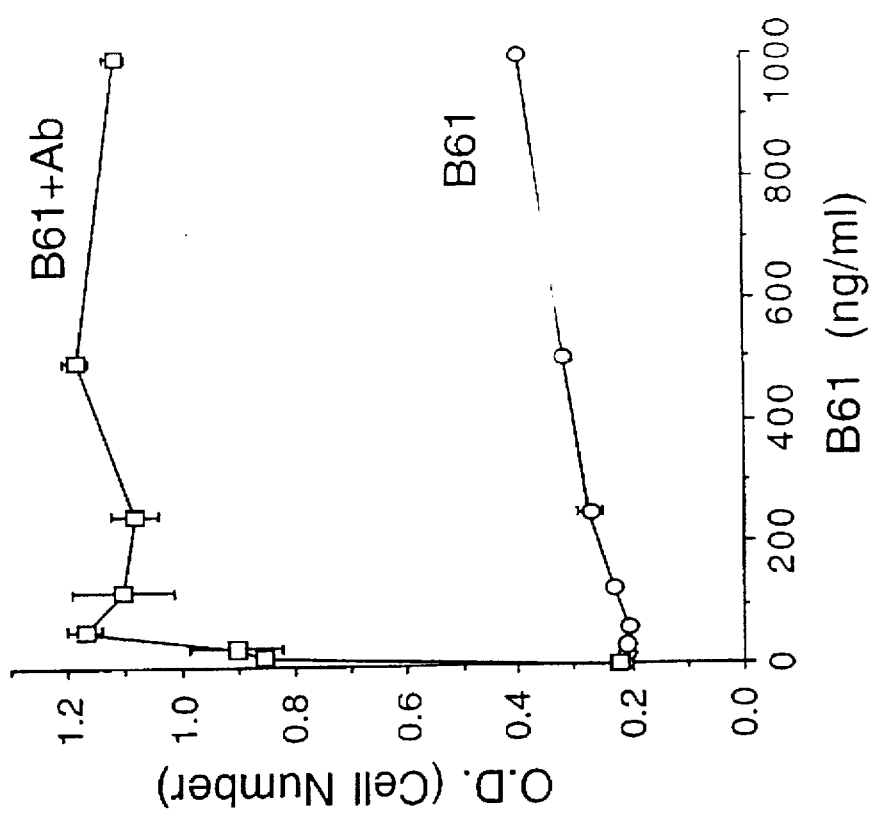
FIG. 6. Induction of growth responses in BAF cells mediated by Eck receptor chimera: A. Stimulations were with soluble Efl-2 (EHK-1L) produced in COS cells with or without subsequent clustering. B. Stimulations were with soluble Efl-1 (B61) produced in COS cells with or without subsequent clustering.

In each case, one skilled in the art will recognize that the success of clustering will require analysis of the biological activity utilizing bioassays such as those described herein. For example, as shown in FIG. 5, despite the fact that receptor phosphorylation is markedly induced by stimulating receptor expressing reporter cells with COS cells over-expressing membrane forms of the ligands B61, Efl-2 and Efl-3 (FIG. 5A, lanes 1 and 2 ), there is no observable phosphorylation using soluble forms of these ligands (FIG. 5B, lanes 2 and 3, and FIG. 5C, lane 2). However, when secreted forms of the ligands are myc-tagged and antibodies are used to cluster the ligands, the previously inactive soluble ligands strongly induce receptor tyrosine phosphorylation in reporter cells expressing Elk and Ehk-1 receptors (FIG. 5B, lanes 4 and 5, FIG. 5C, lane 3) as well as proliferation in reporter cells expressing an Eck receptor chimera (FIG. 6A).

Figure 7:
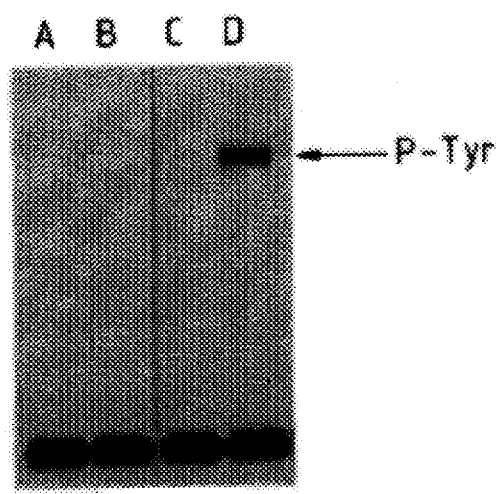
FIG. 7. Induction of ELK receptor tyrosine phosphorylation by clustered but not dimeric ligand. Lane A: mock COS supernatants without anti-human antibodies; Lane B: anti-human antibodies; Lane C: ELK-L-Fc without crosslinking antibodies; and Lane D: crosslinking antibodies. Soluble Fc-tagged ELK ligand (ELK-L-Fc) was produced as COS cell supernatant and used as unclustered dimeric ligand, or ligand clustered by antibodies. Ligand concentrations were estimated by quantitating the amount of Fc epitope using an elisa assay. Ligand clustering was accomplished by adding anti-Human antibodies and incubating at room temperature for 1 hour before stimulating cells. Reporter cells were NIH 3T3 fibroblasts transfected with ELK. Cells were starved for 4–6 hours in serum-free medium, and then stimulated for 40 minutes with: Following stimulation, cells were solubilized and immunoprecipitated with antibodies recognizing the receptors. Immunoprecipitates were immunoblotted with antibodies to phosphotyrosine.

Although in some instances dimerization of the ligand is sufficient to induce biological activity, the data set forth in FIG. 7 demonstrates how, in certain instances, the methods described herein are used to determine the sufficiency of a particular clustering technique. As shown in FIG. 7 with the Elk ligand, dimerization of the soluble ligand utilizing Fc appears to be insufficient for achieving a biological response (FIG. 7, Lane C). Yet, further clustering of the ligand according to the invention using anti-Fc antibodies resulted in a substantial increase in biological activity (lane D).

In the case of the ligand B61, a low level of biological activity appears to be obtained with the soluble ligand achieved without clustering; such low level biological activity may be caused by low level "self-clustering". Regardless, applicants have demonstrated that even in the case of efl's such as B61 that have some biological activity, the activity may be enhanced by clustering according to the present invention.

Cells of the present invention may transiently or, preferably, constitutively and permanently express the Efl's in native form,or in soluble form as tagged Efl's or clustered Efl's as described herein.

The recombinant factors may be purified by any technique which allows for the subsequent formation of a stable, biologically active protein. For example, and not by way of limitation, the factors may be recovered from cells either as soluble proteins or as inclusion bodies, from which they may be extracted quantitatively by 8M guanidinium hydrochloride and dialysis. In order to further purify the factors, conventional ion exchange chromatography, hydrophobic interaction chromatography, reverse phase chromatography or gel filtration may be used.

In additional embodiments of the invention, recombinant efl may be used to inactivate or "knock out" the endogenous gene by homologous recombination, and thereby create an Efl protein deficient cell, tissue, or animal. For example, and not by way of limitation, recombinant efl may be engineered to contain an insertional mutation, for example the neo gene, which would inactivate the native efl gene. Such a construct, under the control of a suitable promoter, may be introduced into a cell, such as an embryonic stem cell, by a technique such as transfection, transduction, injection, etc. Cells containing the construct may then be selected by G418 resistance. Cells which lack an intact efl may then be identified, e.g. by Southern blotting or Northern blotting or assay of expression. Cells lacking an intact efl may then be fused to early embryo cells to generate transgenic animals deficient in such ligand. A comparison of such an animal with an animal expressing endogenous Efl would aid in the elucidation of the role of the ligands in development and maintenance. Such an animal may be used to define specific neuronal populations, or any other in vivo processes, normally dependent upon the ligand.

The present invention also provides for antibodies to the Efl's described herein which are useful for detection of the ligand in, for example, diagnostic applications. Antibodies to the ligands described herein may also be useful for achieving clustering according to the invention. In instances where endogenous ligand exists, the antibody itself may act as the therapeutic by activating existing ligand.

For preparation of monoclonal antibodies directed toward these Efl's, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in "Monoclonal Antibodies and Cancer Therapy," Alan R. Liss, Inc. pp. 77–96) and the like are within the scope of the present invention.

The monoclonal antibodies for diagnostic or therapeutic use may be human monoclonal antibodies or chimeric human-mouse (or other species) monoclonal antibodies. Human monoclonal antibodies may be made by any of numerous techniques known in the art (e.g., Teng et al., 1983, Proc. Natl. Acad. Sci. U.S.A. 80:7308–7312; Kozbor et al., 1983, Immunology Today 4:72–79; Olsson et al., 1982, Meth. Enzymol. 92:3–16). Chimeric antibody molecules may be prepared containing a mouse antigen-binding domain with human constant regions (Morrison et al., 1984, Proc. Natl. Acad. Sci. U.S.A. 81:6851, Takeda et al., 1985, Nature 314:452).

Various procedures known in the art may be used for the production of polyclonal antibodies to epitopes of the Efl's described herein. For the production of antibody, various host animals can be immunized by injection with the Efl's, or a fragment or derivative thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

A molecular clone of an antibody to a selected Efl epitope can be prepared by known techniques. Recombinant DNA methodology (see e.g., Maniatis et al., 1982, Molecular Cloning, A Laboratory Manual, Cold Spring Harbor Laboratory, Cold Spring Harbor, N.Y.) may be used to construct nucleic acid sequences which encode a monoclonal antibody molecule, or antigen binding region thereof.

Antibody molecules may be purified by known techniques, e.g., immunoabsorption or immunoaffinity chromatography, chromatographic methods such as HPLC (high performance liquid chromatography), or a combination thereof, etc.

The present invention provides for antibody molecules as well as fragments of such antibody molecules. Antibody fragments which contain the idiotype of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

The present invention also provides for methods of treating a patient suffering from a neurological disorder comprising treating the patient with an effective amount of one or more Efl's, peptide fragments thereof, or derivatives thereof capable of binding to Ehk-1 or Elk receptor.

The potential therapeutic use of cognate ligands to Ehk-1 were suggested in copending U.S. patent application Ser. No. 08/144,992. In adult brain, cellular localizations of ehk-1 indicated that the gene is primarily expressed in neurons, and reach their highest levels of expression in distinctive neuronal populations that include some of the principal ascending central cholinergic nuclei (interpeduncular region, olfactory tubercle and lateral amygdala) and monoaminergic nuclei (locus coeruleus, dorsal raphe and substantia nigra). Ehk-1 probes strongly highlighted the piriform cortex in the ventrolateral region of the forebrain, the horizontal limb of the diagonal band, the rostral septum and neurons associated with the indusium griseum and tenia tecta, in the hippocampus, in pyramidal neurons in CA3 and CA2, and somewhat weaker in CA1, in the superior colliculus and in retrosplenial cortex and neurons of the locus coeruleus.

In adult rat brain, Ehk-1 can be seen to strongly highlight neuronal rich densities associated with the interpeduncular nuclei and substantia nigra, the basolateral and lateral amygdala and dorsal raphe. Ehk-1 probes were capable of significant hybridization to the granular layer of the cerebellum, in Purkinje cells in the cerebellum and mitral cells in the olfactory bulb.

In E13 embryos, ehk-1 transcripts are noticeably more abundant in head than in body. By post-natal day 1 (P1) the bands reach their highest level in brain, declining slightly in adult brain. Ehk-1 bands decline in cerebellar samples during the transition from P1 to adults, suggesting that the major sites of expression in adult whole brain are predominantly outside the cerebellum.

Longer exposures demonstrate that the ehk-1 neural-specific bands are also detectable in RNAs from primary cultures of hippocampal astrocytes. This is unexpected because RNA in situ hybridization studies indicate that the ehk gene is predominantly expression in neurons, not glia. Examination in various established cell lines has indicated that ehk-1 is predominantly expressed in neuronally derived cells, including various neuroepitheliomal and neuroblastomal lines.

The Elk receptor is also expressed primarily in brain. Accordingly, it is believed that the Elk binding ligand described herein will support the induction of a differential function and/or influence the phenotype, such as growth and/or survival of neural cells, expressing this receptor.

Figure 4B:
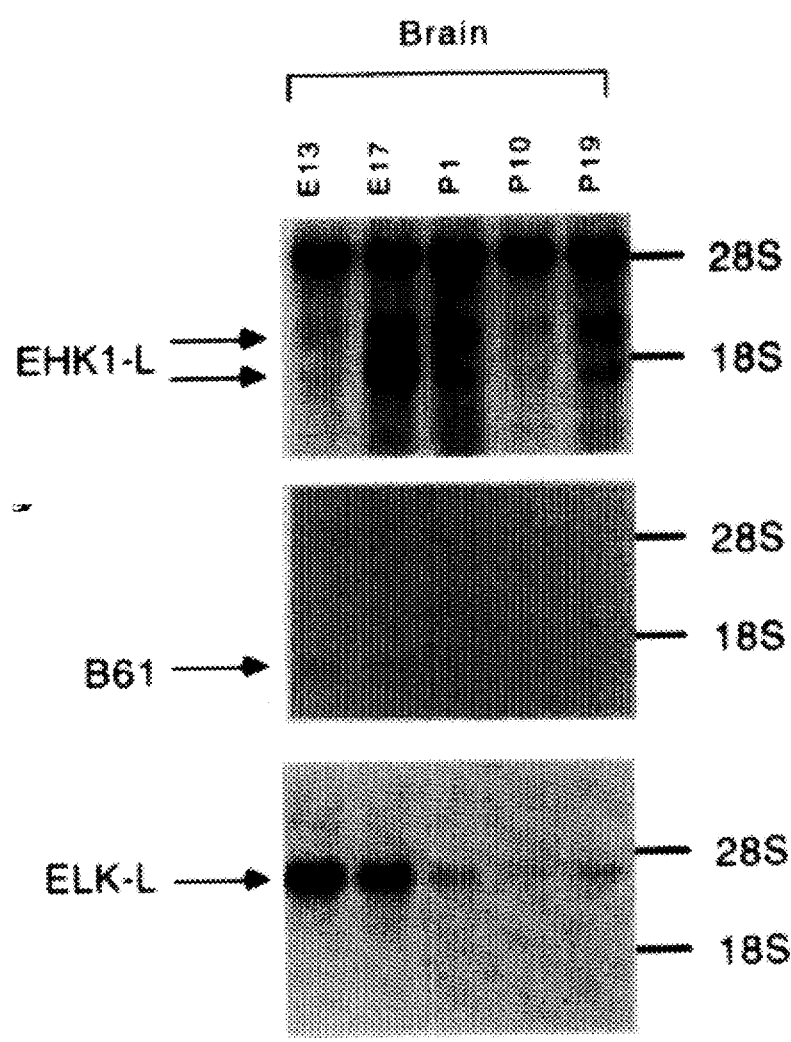
FIG. 4. Northern blot analysis of Efl-1 (B61), Efl-2 (EHK-1L) and Efl-3 (ELK-L) expression in adult rat tissues (A) and in developing brain (B). Total RNA (20 micrograms per lane) was isolated from the indicated tissues, fractionated on 1 percent formaldehyde-agarose gels and transferred to nylon membranes. Blots were hybridized to $^{32}$P-labelled probes derived from restriction fragments internal to the coding regions of each cDNA.

Northern blot analysis (FIG. 4) revealed restricted and reciprocal patterns of expression for Efl-2 (EHK-1L) and Efl-1 (B61), in contrast to broad distribution of Efl-3 (ELK- L). Like Ehk-1, Efl-2 is expressed almost exclusively in the central nervous system, with the notable exception of high expression in skin, where Ehk-1 expression is almost undetectable. In contrast, Efl-1 (B61) is expressed primarily in non-neuronal tissues (FIG. 4A; longer exposures reveal low levels of B61 in most neural structures). Unlike the Elk receptor, which is expressed in only the brain and testes, Efl-3 (ELK-L) is widely expressed in both neuronal and non-neuronal tissues. In brain, expression of both Efl-1 and Efl-3, but not Efl-2, is substantially higher early in development and then decreases (FIG. 4B). As with Efl-1 and Efl-3, the ligands for other nervous-system specific receptor tyrosine kinases (such as the neurotrophin ligands for the Trk receptors) are also expressed in non-neuronal tissues (Maisonpierre, et al. 1990, Science 247:1446–1451; Maisonpierre, et al. 1990, Neuron 5:501–509), apparently because they serve as target-derived factors for axonal processes innervating these tissues (Thoenen, H. 1991, Trends Neurosci. 14:165–170). The non-neuronal expression of Efl-1 and Efl-3 also raises the possibility that they serve as ligands for members of the Eph receptor family, such as Eck, that are expressed by non-neural cells.

The present invention also provides for pharmaceutical compositions comprising the Efl's described herein, peptide fragments thereof, or derivatives in a suitable pharmacologic carrier.

The Efl proteins, peptide fragments, or derivatives may be administered systemically or locally. Any appropriate mode of administration known in the art may be used, including, but not limited to, intravenous, intrathecal, intraarterial, intranasal, oral, subcutaneous, intraperitoneal, or by local injection or surgical implant. Sustained release formulations are also provided for.

As our understanding of neurodegenerative disease/neurotrauma becomes clearer, it may become apparent that it would be beneficial to decrease the effect of endogenous Efl. Therefore, in areas of nervous system trauma, it may be desirable to provide Efl antagonists, including, but not limited to, soluble forms of Efl's which may compete with cell-bound ligand for interaction with Ehk-1 or Elk receptor. Alternatively, soluble forms of the Ehk, Eck or Elk receptors (e.g. expressed as "receptorbodies" produced as described in Example 1 herein) may act as antagonists by binding, and thereby inactivating the ligand. It may be desirable to provide such antagonists locally at the injury site rather than systemically. Use of an Efl antagonist providing implant may be desirable.

Alternatively, certain conditions may benefit from an increase in Efl responsiveness. It may therefore be beneficial to increase the number or binding affinity of Efl in patients suffering from such conditions. This could be achieved through gene therapy using either Efl, Efl expressing cells, or Ehk-1 or Elk receptor. Selective expression of such recombinant proteins in appropriate cells could be achieved using their encoding genes controlled by tissue specific or inducible promoters or by producing localized infection with replication defective viruses carrying the recombinant genes.

EXAMPLE 1

Expression Cloning of Ehk-1 Binding Ligands

COS-7 cells were cultured in Dulbecco's modified Eagle's medium (DMEM) containing 10% fetal bovine serum (FBS), 1% each of penicillin and streptomycin (P/S) and 2 mM glutamine in an atmosphere of 5% $CO_2$. The human neuroblastoma cell line, SH-SY5Y (obtained from June Biedler, Sloan-Kettering) was cultured in Eagle's minimal essential medium (EMEM) with 10% FBS, (P/S) and 2 mM glutamine. Full length human Efl cDNA clones were obtaining by screening a SHSY5Y cDNA library in the pJFE14 vector expressed in COS cells. This vector, as shown in FIG. 1, is a modified version of the vector pSR$_\alpha$ (Takebe, et al. 1988, Mol. Cell. Biol. 8:466–472). The library was created using the two BSTX1 restriction sites in the pJFE14 vector.

COS-7 cells were transiently transfected with either the pJFE14 library or control vector by the DEAE-dextran transfection protocol. Briefly, COS-M5 cells were plated at a density of $1.0 \times 10^6$ cells per 100 mm plate 24 hours prior to transfection. For transfection, the cells were cultured in serum-free DMEM containing 400 μg/ml of DEAE-dextran, 1 μM chloroquine, and 2 mM glutamine, and 1 μg of the appropriate DNA for 3–4 hours at 37° C. in an atmosphere of 5% $CO_2$. The transfection media was aspirated and replaced with phosphate-buffered saline with 10% DMSO for 2–3 min. Following this DMSO "shock", the COS-7 cells were placed into DMEM with 10% FBS, 1% each of penicillin and streptomycin, and 2 mM glutamine for 48 hours.

The screening was conducted by direct localization of surface staining using an Ehk-1 receptorbody, which consisted of the extracellular domain of Ehk-1 fused to the IgG1 constant region. This receptorbody was prepared as follows: The Fc portion of human IgG1, starting from the hinge region and extending to the carboxy terminus of the molecule, was cloned from placental cDNA using PCR with oligonucleotides corresponding to the published sequence of human IgG1 Convenient restriction sites were also incorporated into the oligonucleotides so as to allow cloning of the PCR fragment into an expression vector. Expression vectors containing full length receptors were modified either by restriction enzyme digests or by PCR strategies so as to replace the transmembrane and intracellular domains with restriction sites that allow cloning the human IgG1 fragment into these sites; this was done in such a way as to generate a fusion protein with the receptor ectodomain as its amino-terminus and the Fc portion of human IgG1 as its carboxy-terminus. An alternative method of preparing receptorbodies is described in Goodwin, et. al. 1993, Cell 73:447–456).

Briefly, a 100 mm dish of COS cells was transfected with 1 μg of SHSY5Y library plasmid DNA. Two days after transfection, the cells were probed by incubating them for 30 min with Ehk-1IgG (in the form of COS cell supernatants). The cells were then washed twice with PBS, fixed with methanol, and then incubated for an additional 30 min with PBS/10% Bovine Calf Serum/anti-human IgG-alkaline phosphatase conjugate. After three PBS washes, cells were incubated in alk-phos substrate for 30–60 min. The dish was then inspected microscopically for the presence of surface-stained cells. For each stained cell a small area surrounding it was scraped from the dish using a plastic pipette tip and plasmid DNA was then rescued and used to electroporate bacterial cells. Plasmid DNA prepared from cultures derived from these electroporations was used to transfect COS cells for a second round of enrichment. The second round was performed with standard panning techniques. After the second round of enrichment, single bacterial colonies were picked and plasmid DNA prepared from these colonies was tested for its ability to induce Ehk-1 staining in COS cells transfected with them.

Three clones were identified that exhibited binding to the Ehk-1 receptorbody. The first was identified as B61. The second and third clone, which are identical, and designated herein as Efl-2, appear to be different, but related to B61, as determined using partial nucleotide sequencing, suggesting that these may be family members of B61. All three ligands appear to be membrane bound. Further, like B61, Efl-2 is GPI-linked.

EXAMPLE 2

Cloning of Novel Efl's

Regions of homology between B61 and Efl-2 can be used to identify additional Efl's as described in U.S. patent application Ser. No. 08/144,992. For example, FIG. 2 reveals two such regions of sequence homology that respectively bear the single letter amino acid sequences, V(F/Y) WNSSN (SEQ ID NO:2) and NDY(V/L)DI(I/Y)CPHY (SEQ ID NO: 3), where letters in parenthesis indicate residues that differ in human and rat B61 as compared to the deduced Efl-2 protein. Degenerate oligodeoxynucleotides corresponding to these conserved protein regions can then be designed and used to prime PCR reactions using cDNAs made from various tissues, including embryonic and adult brain. Resulting amplified DNA fragments can then be cloned by insertion into plasmids, subjected to DNA sequencing and these sequences may then be compared with those of the known Efl's.

EXAMPLE 3

Expression Cloning of Elk Binding Ligand

COS-7 cells were cultured in Dulbecco's modified Eagle's medium (DMEM) containing 10% fetal bovine serum (FBS), 1% each of penicillin and streptomycin (P/S) and 2 mM glutamine in an atmosphere of 5% $CO_2$. The human neuroepithelioma line CHP100 (obtained from ) was cultured in Eagle's minimal essential medium (EMEM) with 10% FBS, (P/S) and 2 mM glutamine.

Full length human Efl cDNA clones were obtaining by screening a CHP100 cDNA library in the pJFE14 vector expressed in COS cells. This vector, as shown in FIG. 1, is a modified version of the vector $pSR_\alpha$ (Takebe, et al. 1988, Mol. Cell. Biol. 8:466–472). The library was created using the two BSTX1 restriction sites in the pJFE14 vector.

COS-7 cells were transiently transfected with either the pJFE14 library or control vector by the DEAE-dextran transfection protocol. Briefly, COS-M5 cells were plated at a density of $1.0 \times 10^6$ cells per 100 mm plate 24 hours prior to transfection. For transfection, the cells were cultured in serum-free DMEM containing 400 µg/ml of DEAE-dextran, 1 µM chloroquine, and 2 mM glutamine, and 1 µg of the appropriate DNA for 3–4 hours at 37° C. in an atmosphere of 5% $CO_2$. The transfection media was aspirated and replaced with phosphate-buffered saline with 10% DMSO for 2–3 min. Following this DMSO "shock", the COS-7 cells were placed into DMEM with 10% FBS, 1% each of penicillin and streptomycin, and 2 mM glutamine for 48 hours.

The screening was conducted by direct localization of surface staining using an Elk receptorbody, which consisted of the extracellular domain of Elk fused to the IgG1 constant region. This receptorbody was prepared as follows: The Fc portion of human IgG1, starting from the hinge region and extending to the carboxy terminus of the molecule, was cloned from placental cDNA using PCR with oligonucleotides corresponding to the published sequence of human IgG 1. Convenient restriction sites were also incorporated into the oligonucleotides so as to allow cloning of the PCR fragment into an expression vector. Expression vectors containing full length receptors were modified either by restriction enzyme digests or by PCR strategies so as to replace the transmembrane and intracellular domains with restriction sites that allow cloning the human IgG1 fragment into these sites; this was done in such a way as to generate a fusion protein with the receptor ectodomain as its amino-terminus and the Fc portion of human IgG1 as its carboxy-terminus. An alternative method of preparing receptorbodies is described in Goodwin, et. al. 1993, Cell 73:447–456).

Briefly, a 100 mm dish of COS cells was transfected with 1µg of CHP100 library plasmid DNA. Two days after transfection, the cells were probed by incubating them for 30 min with Elk-IgG (in the form of COS cell supernatants). The cells were then washed twice with PBS, fixed with methanol, and then incubated for an additional 30 min with PBS/10% Bovine Calf Serum/anti-human IgG-alkaline phosphatase conjugate. After three PBS washes, cells were incubated in alk-phos substrate for 30–60 min. The dish was then inspected microscopically for the presence of surface-stained cells. For each stained cell a small area surrounding it was scraped from the dish using a plastic pipette tip and plasmid DNA was then rescued and used to electroporate bacterial cells. Plasmid DNA prepared from cultures derived from these electroporations was used to transfect COS cells for a second round of enrichment. The second round was performed with standard panning techniques. After the second round of enrichment, single bacterial colonies were picked and plasmid DNA prepared from these colonies was tested for its ability to induce Elk staining in COS cells transfected with them.

A clone identified that exhibited binding to the Elk receptorbody was deposited with the ATCC on Apr. 12, 1994 and designated as 75734.

EXAMPLE 4

Activation of Soluble Efl's

Assays of membrane bound Efl's were conducted by growing either COS cells transfected with vector alone (COS-Mock) or COS cells transfected with Efl-3 expression vector, detaching the cells from the dishes with PBS+1 mM EDTA, pelleting, and resuspending in PBS. The cells were layered on top of reporter cell lines.

Soluble Efl-3 and B61, each tagged using the myc epitope at their C-termini [Stahl, et al. Science 263, 92–95 (1994)], were produced as COS cell supernatants and used as unclustered ligands or ligands clustered by antibodies. Ligand concentrations were estimated by quantitating the amount of myc epitope on slot blots; ligand clustering was accomplished by adding anti-myc monoclonal antibodies and anti-mouse polyclonal antibodies and incubating at 37° C. for 1 hour before stimulating cells. Reporter cell lines were 3T3 fibroblasts transfected with Elk (FIGS. 5A and 5B) or C2C12 cells transfected with Ehk-1 (FIG. 5C). Reporter cells on 10 cm dishes were starved for 4–6 hours in serum-free medium and then stimulated for 15 minutes as noted above, then solubilized and immunoprecipitated with antibodies recognizing the receptors. Immunoprecipitates were immunoblotted with antibodies to phosphotyrosine (FIG. 5, UPPER PANELS), and subsequently stripped and reprobed with antibodies recognizing the receptors to visualize total receptor protein (FIG. 5, LOWER PANELS).

Figure 9:
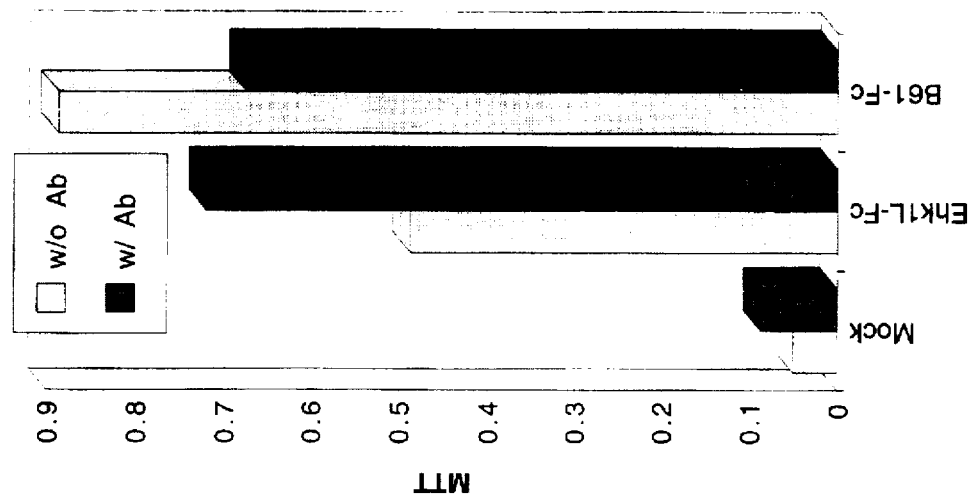
FIG. 9. Induction of growth responses in BAF cells mediated by ECK receptor chimera. Stimulations were performed with soluble EHK1-L-Fc and B61-Fc produced in COS cells with or without subsequent clustering with anti-human antibodies.
Figure 8:
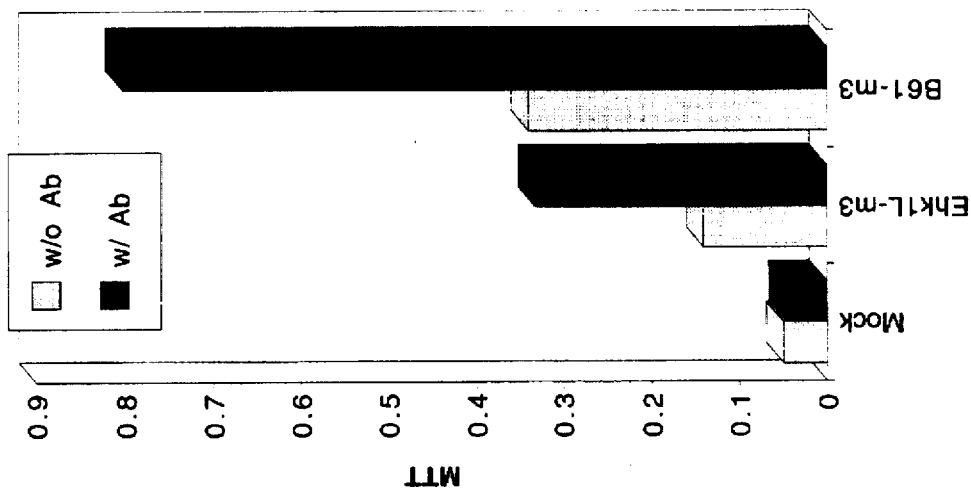
FIG. 8. Induction of growth responses in BAF cells mediated by ECK receptor chimera. Stimulations were performed with soluble triple myc-tagged EHK1 ligand (EHK1L-m3) and triple myc-tagged B61 (B61-m3) produced in COS cells with or without subsequent clustering with anti-myc and anti-mouse antibodies. Because the catalytic domain of ECK receptor does not mediate growth response in BAF cells, a receptor chimera (in which the ectodomain of the ECK receptor was fused to the cytoplasmic domain of the FGF receptor) was instead introduced into BAF cells to make the reporter cell line.

To measure induction of growth responses in BAF cells mediated by Eck receptor chimera, stimulations were made with soluble Efl-1 and B61, produced in COS cells with or without subsequent clustering. After two days of stimulation the number of viable cells was assessed by adding the vital dye MTT (3-{4,5-dimethylthiazol-2-yl}-2,5-diphenyltetrazolium bromide) for 4 hours, followed by solubilization and determination of optical density (O.D.), as previously described [Ip, et al., 1993, Neuron 10:137–149] (FIG. 8). The data described in FIG. 9 results from MTT assays performed as above with soluble Ehk-1L-Fc and B61-Fc produced in COS cells with and without subsequent clustering with anti-Fc antibodies. Because the catalytic domain of the Eck receptor does not mediate growth responses in BAF cells, a receptor chimera (in which the ectodomain of the Eck receptor was fused to the cytoplasmic domain of the FGF receptor) was instead introduced into BAF cells to make a reporter cell line.

As shown in FIG. 5B, lanes 2 and 3, and FIG. 5C, lane 2, no ligand-induced receptor activation, as judged by receptor phosphorylation, was observed using soluble forms of Efl-3 or B61. However, receptor phosphorylation was markedly induced by stimulating receptor expressing reporter cells with COS cells overexpressing membrane-bound forms of these ligands (e.g. FIG. 5A, lanes 1 and 2). To explain this discrepancy, we speculated that membrane attachment facilitates ligand clustering, which in turn promotes receptor multimerization and activation. To mimic ligand clustering in solution, secreted forms of the ligands were constructed with epitope tags added at their C-termini; antibodies against the tags were then used to aggregate the ligands. This type of clustering enabled previously inactive soluble ligands to strongly induce receptor tyrosine phosphorylation in reporter cells expressing Elk and Ehk-1 receptors (FIG. 5B, lanes 1–5 and FIG. 5C, lanes 1–3). Similarly, as shown in FIG. 7, with respect to Efl-3 (ELK-L), dimerization of the ligand is insufficient to induce biological active, whereas multimers had significant activity. These results demonstrate the need, as described herein, to assess the efficacy of a particular mechanism of clustering insofar as each particular ligand is concerned.

Figure 6B:
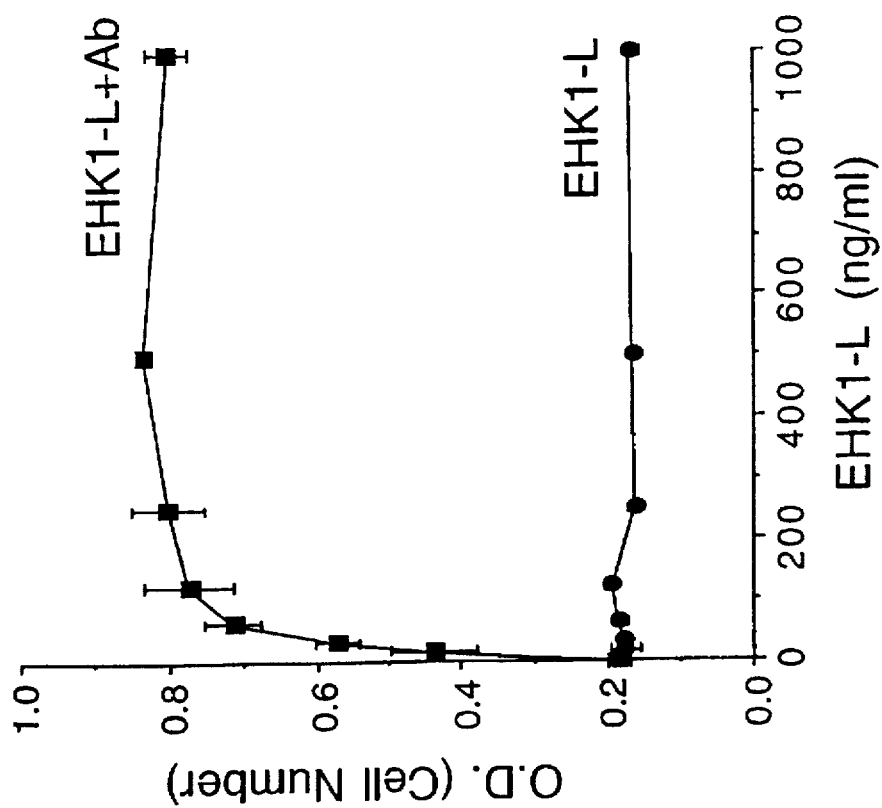

Such efficacy of the clustering may be determined by measuring phosphorylation of the receptor. Alternatively, proliferation in reporter cells expressing an appropriate receptor or receptor chimera, such as the Eck receptor chimera utilized in experiments the results of which are shown in FIG. 6.

Dose-response studies demonstrated that clustering resulted in at least 100-fold greater potency, and saturable responses with low concentrations of ligand (comparable to those seen with ligands for other receptor families [Ip, et al. Neuron 10:137–149 (1993)], in both the phosphorylation assay (tested for the Elk ligand, data not shown) and in the proliferation assay (tested for Efl-1 and B61, FIG. 6). The small effect of unclustered B61 (FIG. 6B) is reminiscent of the recent finding that high concentrations of soluble B61 could induce Eck tyrosine phosphorylation [Bartley, et al. Nature 368:558–560 (1994); in the latter study, saturation was not achieved even at 1–2 mg/ml concentrations of B61. These effects might be attributed to a weak ability of the soluble ligand itself to dimerize or aggregate, either spontaneously or as a result of purification. Soluble ligands are thought to activate their receptors by virtue of being bivalent or multivalent [Schlessinger, J. & Ullrich, A. Neuron 9:383–391 (1992)]; some ligands are monomers that contain two distinct receptor binding sites, while others achieve bivalency as covalent or non-covalently linked dimers. Our results define a new class of ligands that seem ineffective as soluble ligands, possibly because they are monovalent, although they can be artificially activated in solution by clustering. These ligands seem to depend on their membrane attachment to aggregate and activate their receptors. By limiting diffusion to two dimensions, membrane attachment could simply increase the likelihood of ligand—ligand collisions and thereby promote ligand dimerization, or more extensive ligand clustering, among ligands that interact only weakly in solution. Alternatively, specific mechanisms may exist to create cell-surface ligand clusters. In addition, ligand-receptor pairs would be expected to accumulate in areas of contact between cells bearing ligands and cells bearing receptors.

Any or all of these lateral aggregation effects could contribute to receptor multimerization and activation. The observation that the EPH-related, neuronally-expressed NUK receptor transiently concentrates in areas of cell-to-cell contact [Henkemeyer, et al. Oncogene 9:1001–1014 (1994)], supports the possibility that interactions between ligand bound to one membrane and receptor bound to another membrane could promote lateral aggregation.

Deposit of Microorganisms

The following microorganisms have been deposited with the American Type Culture Collection, 12301 Parklawn Drive, Rockville, Md. 20852 in accordance with the Budapest Treaty.

|  | ACCESSION NUMBER |
| --- | --- |
| pJFE14 containing efl-2 | 75728 |
| pJFE14 containing efl-3 | 75734 |

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various references are cited herein, the disclosures of which are incorporated by reference in their entireties.

What is claimed is:

1. A method of activating an Elk, Ehk or Eck receptor comprising stimulating said receptor with a composition comprising clustered (soluble Efl)$_n$, wherein the soluble Efl is the extracellular domain of a ligand that binds the Elk, Ehk or Eck receptor and n is 2 or greater, with the exception that the soluble Efl is not the extracellular domain of Elk-L.

2. A method of activating an Elk, Ehk or Eck receptor comprising treating the receptor with a tagged soluble ligand that binds to said Elk, Ehk or Eck receptor which has been clustered using anti-tag antibody.

3. A method according to claim 2 wherein said tag is myc or the Fc domain of an immunoglobulin.

4. A purified composition comprising tagged extracellular domain of a ligand that binds to an Elk, Ehk or Eck receptor and an anti-tag antibody.

5. A composition according to claim 4 further comprising a suitable pharmacologic carrier.

6. A composition according to claim 4 wherein said tag is myc or the Fc domain of an immunoglobulin.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:

(A) LENGTH: 6 amino acids
(B) TYPE: amino acid
(C) STRANDEDNESS:
(D) TOPOLOGY: unknown (ii) MOLECULE TYPE: peptide (xi) SEQUENCE DESCRIPTION: SEQ ID NO:1:

His His His His His His
1               5

(2) INFORMATION FOR SEQ ID NO:2:

(i) SEQUENCE CHARACTERISTICS:
(A) LENGTH: 7 amino acids
(B) TYPE: amino acid
(C) STRANDEDNESS:
(D) TOPOLOGY: unknown (ii) MOLECULE TYPE: peptide (ix) FEATURE:
(A) NAME/KEY: Peptide
(B) LOCATION: 2
(D) OTHER INFORMATION: /label=A
/ note= "X can represent either phenylalanine or tyrosine."

(xi) SEQUENCE DESCRIPTION: SEQ ID NO:2:

Val Xaa Trp Asn Ser Ser Asn
1               5

(2) INFORMATION FOR SEQ ID NO:3:

(i) SEQUENCE CHARACTERISTICS:
(A) LENGTH: 11 amino acids
(B) TYPE: amino acid
(C) STRANDEDNESS:
(D) TOPOLOGY: unknown (ii) MOLECULE TYPE: peptide (ix) FEATURE:
(A) NAME/KEY: Peptide
(B) LOCATION: 4
(D) OTHER INFORMATION: /label=A
/ note= "X can represent either valine or leucine."

(ix) FEATURE:
(A) NAME/KEY: Peptide
(B) LOCATION: 7
(D) OTHER INFORMATION: /label=B
/ note= "X can represent either isoleucine or tyrosine."

(xi) SEQUENCE DESCRIPTION: SEQ ID NO:3:

Asn Asp Tyr Xaa Asp Ile Xaa Cys Pro His Tyr
1               5                   10

(2) INFORMATION FOR SEQ ID NO:4:

(i) SEQUENCE CHARACTERISTICS:
(A) LENGTH: 205 amino acids
(B) TYPE: amino acid
(C) STRANDEDNESS:
(D) TOPOLOGY: unknown (ii) MOLECULE TYPE: protein (xi) SEQUENCE DESCRIPTION: SEQ ID NO:4:

Met Glu Phe Leu Trp Ala Pro Leu Leu Gly Leu Cys Cys Ser Leu Ala
1               5                   10                  15

```
Ala  Ala  Asp  Arg  His  Thr  Val  Phe  Trp  Asn  Ser  Ser  Asn  Pro  Lys  Phe
               20                   25                        30

Arg  Asn  Glu  Asp  Tyr  Thr  Ile  His  Val  Gln  Leu  Asn  Asp  Tyr  Val  Asp
          35                        40                   45

Ile  Ile  Cys  Pro  His  Tyr  Glu  Asp  His  Ser  Val  Ala  Asp  Ala  Ala  Met
          50                        55                   60

Glu  Gln  Tyr  Ile  Leu  Tyr  Leu  Val  Glu  His  Glu  Tyr  Gln  Leu  Cys
65                            70                   75                        80

Gln  Pro  Gln  Ser  Lys  Asp  Gln  Val  Arg  Trp  Gln  Cys  Asn  Arg  Pro  Ser
                    85                        90                        95

Ala  Lys  His  Gly  Pro  Glu  Lys  Leu  Ser  Glu  Lys  Phe  Gln  Arg  Phe  Thr
                    100                       105                       110

Pro  Phe  Thr  Leu  Gly  Lys  Glu  Phe  Lys  Glu  Gly  His  Ser  Tyr  Tyr  Tyr
               115                       120                  125

Ile  Ser  Lys  Pro  Ile  His  Gln  His  Glu  Asp  Arg  Cys  Leu  Arg  Leu  Lys
          130                       135                  140

Val  Thr  Val  Ser  Gly  Lys  Ile  Thr  His  Ser  Pro  Gln  Ala  His  Val  Asn
145                       150                       155                       160

Pro  Gln  Glu  Lys  Arg  Leu  Ala  Ala  Asp  Asp  Pro  Glu  Val  Arg  Val  Leu
                    165                       170                       175

His  Ser  Ile  Gly  His  Ser  Ala  Ala  Pro  Arg  Leu  Phe  Pro  Leu  Ala  Trp
               180                       185                       190

Thr  Val  Leu  Leu  Leu  Pro  Leu  Leu  Leu  Leu  Gln  Thr  Pro
               195                       200                  205
```

( 2 ) INFORMATION FOR SEQ ID NO:5:

( i ) SEQUENCE CHARACTERISTICS:
      ( A ) LENGTH: 234 amino acids
      ( B ) TYPE: amino acid
      ( C ) STRANDEDNESS:
      ( D ) TOPOLOGY: unknown ( i i ) MOLECULE TYPE: protein ( x i ) SEQUENCE DESCRIPTION: SEQ ID NO:5:

```
Met  Ala  Ala  Ala  Pro  Leu  Leu  Leu  Leu  Leu  Leu  Val  Pro  Val  Pro
1                   5                        10                  15

Leu  Leu  Pro  Leu  Leu  Ala  Gln  Gly  Pro  Gly  Gly  Ala  Leu  Gly  Asn  Arg
               20                       25                        30

His  Ala  Val  Tyr  Trp  Asn  Ser  Ser  Asn  Gln  His  Leu  Arg  Arg  Glu  Gly
          35                        40                        45

Tyr  Thr  Val  Gln  Val  Asn  Val  Asn  Asp  Tyr  Leu  Asp  Ile  Tyr  Cys  Pro
     50                        55                        60

His  Tyr  Asn  Ser  Ser  Gly  Ala  Gly  Pro  Gly  Pro  Gly  Gly  Gly  Ala  Glu
65                       70                        75                       80

Gln  Tyr  Val  Leu  Tyr  Met  Val  Ser  Arg  Asn  Gly  Tyr  Arg  Thr  Cys  Asn
                    85                        90                        95

Ala  Ser  Gln  Gly  Phe  Lys  Arg  Trp  Glu  Cys  Asn  Arg  Pro  His  Ala  Pro
               100                       105                       110

His  Ser  Pro  Ile  Lys  Phe  Ser  Glu  Lys  Phe  Gln  Arg  Tyr  Ser  Ala  Phe
               115                       120                       125

Ser  Leu  Gly  Tyr  Glu  Phe  His  Ala  Gly  His  Ser  Tyr  Tyr  Tyr  Ile  Ser
          130                       135                       140

Thr  Pro  Thr  His  Asn  Leu  His  Trp  Lys  Cys  Leu  Arg  Met  Lys  Val  Phe
145                       150                       155                       160

Val  Cys  Cys  Ala  Ser  Thr  Ser  His  Ser  Gly  Glu  Lys  Pro  Val  Pro  Thr
```

|  | | | | | | 165 | | | | | 170 | | | | | 175 | |
|---|---|---|---|---|---|---|---|---|---|---|---|---|---|---|---|---|---|
| Leu | Pro | Gln | Phe | Thr | Met | Gly | Pro | Asn | Val | Lys | Ile | Asn | Val | Leu | Glu |
|  |  |  | 180 |  |  |  | 185 |  |  |  |  | 190 |  |  |  |
| Asp | Phe | Glu | Gly | Glu | Asn | Pro | Gln | Val | Pro | Lys | Leu | Glu | Lys | Ser | Ile |
|  |  |  | 195 |  |  |  | 200 |  |  |  |  | 205 |  |  |  |
| Ser | Gly | Thr | Ser | Pro | Lys | Arg | Glu | His | Leu | Pro | Leu | Ala | Val | Gly | Ile |
|  | 210 |  |  |  |  | 215 |  |  |  |  | 220 |  |  |  |  |
| Ala | Phe | Phe | Leu | Met | Thr | Phe | Leu | Ala | Ser |  |  |  |  |  |  |
| 225 |  |  |  |  | 230 |  |  |  |  |  |  |  |  |  |  |

( 2 ) INFORMATION FOR SEQ ID NO:6:

( i ) SEQUENCE CHARACTERISTICS:
( A ) LENGTH: 346 amino acids
( B ) TYPE: amino acid
( C ) STRANDEDNESS:
( D ) TOPOLOGY: unknown ( i i ) MOLECULE TYPE: protein ( x i ) SEQUENCE DESCRIPTION: SEQ ID NO:6:

| Met | Ala | Arg | Pro | Gly | Gln | Arg | Trp | Leu | Gly | Lys | Trp | Leu | Val | Ala | Met |
|---|---|---|---|---|---|---|---|---|---|---|---|---|---|---|---|
| 1 |  |  |  | 5 |  |  |  |  | 10 |  |  |  |  | 15 |  |
| Val | Val | Trp | Ala | Leu | Cys | Arg | Leu | Ala | Thr | Pro | Leu | Ala | Lys | Asn | Leu |
|  |  |  | 20 |  |  |  | 25 |  |  |  |  | 30 |  |  |  |
| Glu | Pro | Val | Ser | Trp | Ser | Ser | Leu | Asn | Pro | Lys | Phe | Leu | Ser | Gly | Lys |
|  |  | 35 |  |  |  |  | 40 |  |  |  |  | 45 |  |  |  |
| Gly | Leu | Val | Ile | Tyr | Pro | Lys | Ile | Gly | Asp | Lys | Leu | Asp | Ile | Ile | Cys |
|  | 50 |  |  |  |  | 55 |  |  |  |  | 60 |  |  |  |  |
| Pro | Arg | Ala | Glu | Ala | Gly | Arg | Pro | Tyr | Glu | Tyr | Tyr | Lys | Leu | Tyr | Leu |
| 65 |  |  |  |  | 70 |  |  |  |  | 75 |  |  |  |  | 80 |
| Val | Arg | Pro | Glu | Gln | Ala | Ala | Ala | Cys | Ser | Thr | Val | Leu | Asp | Pro | Asn |
|  |  |  |  | 85 |  |  |  |  | 90 |  |  |  |  | 95 |  |
| Val | Leu | Val | Thr | Cys | Asn | Arg | Pro | Glu | Gln | Glu | Ile | Arg | Phe | Thr | Ile |
|  |  |  | 100 |  |  |  |  | 105 |  |  |  |  | 110 |  |  |
| Lys | Phe | Gln | Glu | Phe | Ser | Pro | Asn | Tyr | Met | Gly | Leu | Glu | Phe | Lys | Lys |
|  |  | 115 |  |  |  |  | 120 |  |  |  |  | 125 |  |  |  |
| His | His | Asp | Tyr | Tyr | Ile | Thr | Ser | Thr | Ser | Asn | Gly | Ser | Leu | Glu | Gly |
|  | 130 |  |  |  |  | 135 |  |  |  |  | 140 |  |  |  |  |
| Leu | Glu | Asn | Arg | Glu | Gly | Gly | Val | Cys | Arg | Thr | Arg | Thr | Met | Lys | Ile |
| 145 |  |  |  |  | 150 |  |  |  |  | 155 |  |  |  |  | 160 |
| Ile | Met | Lys | Val | Gly | Gln | Asp | Pro | Asn | Ala | Val | Thr | Pro | Glu | Gln | Leu |
|  |  |  |  | 165 |  |  |  |  | 170 |  |  |  |  | 175 |  |
| Thr | Thr | Ser | Arg | Pro | Ser | Lys | Glu | Ala | Asp | Asn | Thr | Val | Lys | Met | Ala |
|  |  |  | 180 |  |  |  |  | 185 |  |  |  |  | 190 |  |  |
| Thr | Gln | Ala | Pro | Gly | Ser | Arg | Gly | Ser | Leu | Gly | Asp | Ser | Asp | Gly | Lys |
|  |  | 195 |  |  |  |  | 200 |  |  |  |  | 205 |  |  |  |
| His | Glu | Thr | Val | Asn | Gln | Glu | Lys | Ser | Gly | Pro | Gly | Ala | Ser | Gly |
|  | 210 |  |  |  |  | 215 |  |  |  |  | 220 |  |  |  |
| Gly | Ser | Ser | Gly | Asp | Pro | Asp | Gly | Phe | Phe | Asn | Ser | Lys | Val | Ala | Leu |
| 225 |  |  |  |  | 230 |  |  |  |  | 235 |  |  |  |  | 240 |
| Phe | Ala | Ala | Val | Gly | Ala | Gly | Cys | Val | Ile | Phe | Leu | Leu | Ile | Ile | Ile |
|  |  |  |  | 245 |  |  |  |  | 250 |  |  |  |  | 255 |  |
| Phe | Leu | Thr | Val | Leu | Leu | Leu | Lys | Leu | Arg | Lys | Arg | His | Arg | Lys | His |
|  |  |  | 260 |  |  |  |  | 265 |  |  |  |  | 270 |  |  |
| Thr | Gln | Gln | Arg | Ala | Ala | Ala | Leu | Ser | Leu | Ser | Thr | Leu | Ala | Ser | Pro |
|  |  | 275 |  |  |  |  | 280 |  |  |  |  | 285 |  |  |  |

```
        Lys  Gly  Gly  Ser  Gly  Thr  Ala  Gly  Thr  Glu  Pro  Ser  Asp  Ile  Ile  Ile
             290                      295                      300

Pro  Leu  Arg  Thr  Thr  Glu  Asn  Asn  Tyr  Cys  Pro  His  Tyr  Glu  Lys  Val
        305                      310                      315                      320

Ser  Gly  Asp  Tyr  Gly  His  Pro  Val  Tyr  Ile  Val  Gln  Glu  Met  Pro  Pro
                            325                      330                      335

Gln  Ser  Pro  Ala  Asn  Ile  Tyr  Tyr  Lys  Val
                       340                      345
```

( 2 ) INFORMATION FOR SEQ ID NO:7:

( i ) SEQUENCE CHARACTERISTICS:
        ( A ) LENGTH: 135 amino acids
        ( B ) TYPE: amino acid
        ( C ) STRANDEDNESS:
        ( D ) TOPOLOGY: unknown ( i i ) MOLECULE TYPE: protein ( x i ) SEQUENCE DESCRIPTION: SEQ ID NO:7:

```
        Val  Xaa  Trp  Asn  Ser  Ser  Asn  Pro  Lys  Phe  Xaa  Arg  Xaa  Glu  Gly  Tyr
        1                   5                        10                       15

Thr  Ile  Xaa  Val  Xaa  Xaa  Asn  Asp  Tyr  Leu  Asp  Ile  Ile  Cys  Pro  His
                       20                        25                       30

Tyr  Glu  Xaa  Xaa  Xaa  Xaa  Xaa  Xaa  Xaa  Ala  Gly  Xaa  Xaa  Xaa  Glu  Cys
                       35                        40                       45

Tyr  Xaa  Leu  Tyr  Leu  Val  Xaa  Xaa  Glu  Xaa  Tyr  Xaa  Xaa  Cys  Xaa  Xaa
             50                        55                       60

Xaa  Ser  Xaa  Xaa  Xaa  Val  Arg  Trp  Xaa  Cys  Asn  Arg  Pro  Xaa  Ala  Xaa
        65                       70                        75                       80

His  Xaa  Pro  Ile  Lys  Phe  Ser  Glu  Lys  Phe  Gln  Arg  Phe  Ser  Pro  Phe
                            85                       90                       95

Xaa  Leu  Gly  Xaa  Glu  Phe  Lys  Xaa  Gly  His  Xaa  Tyr  Tyr  Tyr  Ile  Ser
                       100                      105                      110

Thr  Xaa  Xaa  Xaa  Pro  Xaa  His  Xaa  Leu  Glu  Xaa  Arg  Xaa  Xaa  Xaa  Xaa
             115                      120                      125

Cys  Xaa  Leu  Arg  Xaa  Met  Lys
             130                      135
```

( 2 ) INFORMATION FOR SEQ ID NO:8:

( i ) SEQUENCE CHARACTERISTICS:
        ( A ) LENGTH: 1070 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:8:

```
GACCTCGAGA  TCCATTGTGC  TGGAAAGGCG  GCGGCGGCTC  CGGGGATGGC  GGCGGCTCCG     60

CTGCTGCTGC  TGCTGCTGCT  CGTGCCCGTG  CCGCTGCTGC  CGCTGCTGGC  CCAAGGGCCC    120

GGAGGGGCGC  TGGGAAACCG  GCATGCGGTG  TACTGGAACA  GCTCCAACCA  GCACCTGCGG    180

CGAGAGGGCT  ACACCGTGCA  GGTGAACGTG  AACGACTATC  TGGATATTTA  CTGCCCGCAC    240

TACAACAGCT  CGGGGGCGGG  ACCGGGGCCC  GGAGGCGGGG  CAGAGCAGTA  CGTGCTGTAC    300

ATGGTGAGCC  GCAACGGCTA  CCGCACCTGC  AACGCCAGCC  AGGGCTTCAA  GCGCTGGGAG    360

TGCAACCGGC  CGCACGCCCC  GCACAGCCCC  ATCAAGTTCT  CGGAGAAGTT  CCAGCGCTAC    420
```

| | | | | | |
|---|---|---|---|---|---|
| AGCGCCTTCT | CTCTGGGCTA | CGAGTTCCAC | GCCGGCCACG | AGTACTACTA | CATCTCCACG | 480 |
| CCCACTCACA | ACCTGCACTG | GAAGTGTCTG | AGGATGAAGG | TGTTCGTCTG | CTGCGCCTCC | 540 |
| ACATCGCACT | CCGGGGAGAA | GCCGGTCCCC | ACTCTCCCCC | AGTTCACCAT | GGGCCCCAAT | 600 |
| GTGAAGATCA | ACGTGCTGGA | AGACTTTGAG | GGAGAGAACC | CTCAGGTGCC | CAAGCTTGAG | 660 |
| AAGAGCATCA | GCGGGACCAG | CCCCAAACGG | GAACACCTGC | CCCTGGCCGT | GGGCATCGCC | 720 |
| TTCTTCCTCA | TGACGTTCTT | GGCCTCCTAG | CTCTGCCCCC | TCCCTGGGG | GGGAGAGAT | 780 |
| GGGGCGGGGN | TTGGAAGGAG | NAGGGAGCCT | TTGGCCTCTC | CAAGGGAAGC | CTAGTGGGCC | 840 |
| TAGACCCCTC | CTCCCATGGT | TAGAAGTGGG | GCCTGNACCA | TACATCTGTG | TCCGCCCCCT | 900 |
| CTACCCCTTC | CCCCCANGTA | GGGNACTGTA | GTGGACCAAG | CACGGNGACA | GACATGGNTC | 960 |
| CCGGGNGGGC | TTGTGGCTCT | GGTAATGTNT | GGCACCAAAC | TTGGGGGGCA | AAAAGGGGAG | 1020 |
| TGCTCAGGAC | TCCCTGGNCC | CTGGTACTTT | CCCTGAATCT | GGTGCCTCTC | | 1070 |